United States Patent
Aumalis et al.

(10) Patent No.: US 11,559,457 B1
(45) Date of Patent: Jan. 24, 2023

(54) ROTATIONAL SWING SYSTEMS AND METHODS FOR PROVIDING VESTIBULAR STIMULATION

(71) Applicants: Deana Jo Aumalis, Madison, AL (US); Stephanie Rose Krueger, Brooklyn, WI (US); Haley B. Brunick, Huntsville, AL (US); Chris Kelley, Athens, AL (US); Scott Banwell, Madison, AL (US); Michael E. Langley, Jr., New Market, AL (US); Christina Carmen, Madison, AL (US)

(72) Inventors: Deana Jo Aumalis, Madison, AL (US); Stephanie Rose Krueger, Brooklyn, WI (US); Haley B. Brunick, Huntsville, AL (US); Chris Kelley, Athens, AL (US); Scott Banwell, Madison, AL (US); Michael E. Langley, Jr., New Market, AL (US); Christina Carmen, Madison, AL (US)

(73) Assignee: Board of Trustees of the University of Alabama, for and on behalf of the University of Alabama in Huntsville, Huntsville, AL (US)

(*) Notice: Subject to any disclaimer, the term of this patent is extended or adjusted under 35 U.S.C. 154(b) by 690 days.

(21) Appl. No.: 16/589,073

(22) Filed: Sep. 30, 2019

Related U.S. Application Data

(60) Provisional application No. 62/821,160, filed on Mar. 20, 2019.

(51) Int. Cl.
*A61H 1/00* (2006.01)
*A61M 21/02* (2006.01)
*A61M 21/00* (2006.01)

(52) U.S. Cl.
CPC ............. *A61H 1/005* (2013.01); *A61M 21/02* (2013.01); *A61H 2201/0149* (2013.01);
(Continued)

(58) Field of Classification Search
CPC ....... A61H 1/001; A61H 1/005; A61M 21/00; A61M 21/02
See application file for complete search history.

(56) References Cited

U.S. PATENT DOCUMENTS 2,956,632 A     10/1960   Forbush et al.
4,304,437 A  *  12/1981   Longo ................. A47C 3/0255
                                                    297/277
(Continued)

OTHER PUBLICATIONS

Squirrel Products, (2019), https://www.amazon.com/gp/product/B07212XTKV/ref=oh_aui_detailpage_o02_s00?ie=UTF8&psc=1.
(Continued)

*Primary Examiner* — John P Lacyk
(74) *Attorney, Agent, or Firm* — Maynard Cooper & Gale, P.C.; Jon E. Holland

(57) ABSTRACT

A rotational swing system is used for providing vestibular stimulation. The rotational swing system may include a rotational swing that is actuated by a motor. The system has a support frame arranged so that the motor does not need to bear the weight of the swing, thereby reducing the cost of the motor. When the system is used in a classroom to provide vestibular stimulation to a child with Autism Spectrum Disorder (ASD), the automatic actuation of the swing by the motor helps to free the teacher's attention for addressing the needs of the other children in the classroom.

25 Claims, 8 Drawing Sheets

(52) U.S. Cl.
CPC ............... *A61H 2201/1671* (2013.01); *A61H 2203/0431* (2013.01); *A61M 2021/0005* (2013.01)

(56) References Cited

U.S. PATENT DOCUMENTS

| | | | | |
|---|---|---|---|---|
| 4,825,855 | A | * | 5/1989 | Kundson, Jr. ............. A61F 6/02 600/38 |
| 5,161,522 | A | * | 11/1992 | Clevenger ............ A61G 5/1091 601/24 |
| 5,376,053 | A | | 12/1994 | Ponder et al. |
| 5,782,243 | A | * | 7/1998 | Bisyak ................... A61H 19/50 600/38 |
| 8,182,356 | B2 | * | 5/2012 | Hylton ..................... A61H 1/02 472/118 |
| 2009/0105002 | A1 | | 4/2009 | Kahn et al. |

OTHER PUBLICATIONS

Title Boxing, (2019), https://www.titleboxing.com/punching-bags/bag-stands-accessories/heavy-bag-stands/title-adjustable-heavy-duty-heavy-bag-stand.

* cited by examiner

ROTATIONAL SWING SYSTEMS AND METHODS FOR PROVIDING VESTIBULAR STIMULATION

CROSS REFERENCE TO RELATED APPLICATION

This application claims priority to U.S. Provisional Application No. 62/821,160, entitled "Rotational Swing Systems and Methods for Providing Vestibular Stimulation" and filed on Mar. 20, 2019, which is incorporated herein by reference.

RELATED ART

Autism Spectrum Disorder (ASD) is a neurological disorder occurring in early childhood that creates behavioral and communication problems, thereby adversely affecting an autistic child's ability to learn and interact socially with others. Children with ASD are often treated on a case-by-case basis with various treatments, including speech therapy, behavioral and communication therapy, music therapy, etc.

Many children diagnosed with Autism Spectrum Disorder tend to have a dysfunctional sensory system making them either hyposensitive or hypersensitive to sensory stimulation. It can be difficult for such children to perform certain activities or remain focused through therapeutic or educational sessions. Hence, sensory integration activities, such as vestibular stimulation, are often performed in an effort to regulate the child's sensory system. For example, it has been shown that providing vestibular stimulation to a child with ASD through rotational spinning, which affects pressures within the child's inner ear, has a calming effect that helps to improve the child's behavior and interaction with others. Thus, when a child with ASD begins to exhibit behavioral or communication problems in a classroom, the teacher may place the child on a rotating chair and gently spin the child in the chair for a period of time. This technique is often effective in improving the child's behavior and focus, but it can divert the attention of the teacher from the needs of the other children in the classroom. Improved techniques for providing vestibular stimulation to children with ASD are generally desired. It is generally desirable for systems used for vestibular stimulation to be reliable and inexpensive in order to facilitate their adoption into the marketplace.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

FIG. 4b depicts a side view of the upper bearing plate depicted by FIG. 4a.

FIG. 5b depicts a top view of the lower bearing plate depicted by FIG. 5a.

FIG. 6b depicts a side view of the connector depicted by FIG. 6a.

FIG. 7b depicts a top view of the coupler depicted by FIG. 7a.

FIG. 8b depicts a side view of the bearing depicted by FIG. 8a.

DETAILED DESCRIPTION

The present disclosure generally relates to rotational swing systems and methods for providing vestibular stimulation. In an exemplary embodiment, a rotational swing system includes a rotational swing that is actuated by a motor. The system has a support frame arranged so that the motor does not need to bear the weight of the swing, thereby reducing the cost of the motor. When the system is used in a classroom to provide vestibular stimulation to a child with Autism Spectrum Disorder (ASD), the automatic actuation of the swing by the motor helps to free the teacher's attention for addressing the needs of the other children in the classroom.

Figure 1:
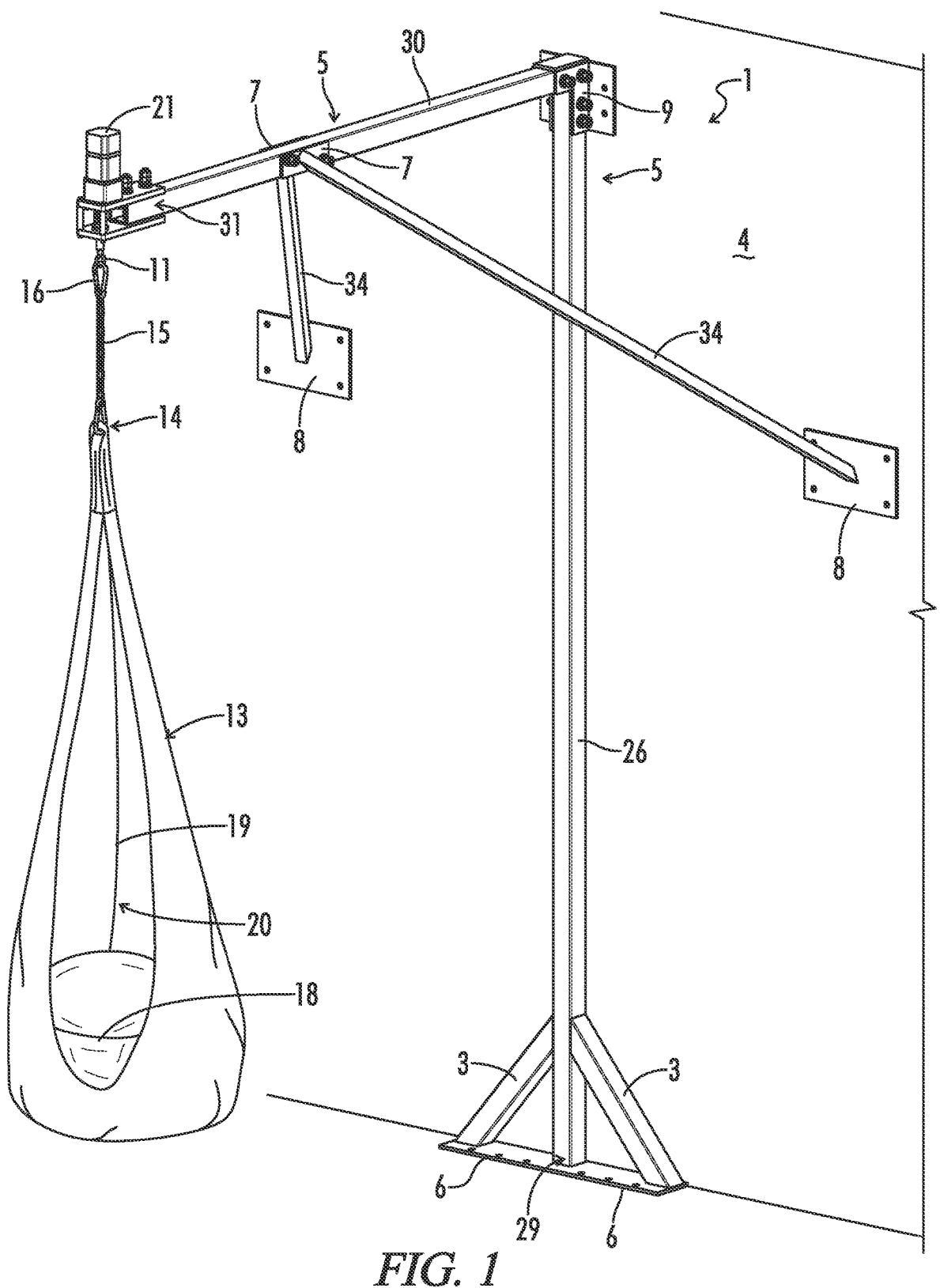
FIG. 1 depicts an exemplary embodiment of a rotational swing system having a hammock swing for a spinning a user, such as a child with ASD, in order to provide vestibular stimulation.

FIG. 1 depicts an exemplary embodiment of a rotational swing system 1. The system 1 comprises a support frame 5 that has a base 6 for supporting the system 1. In the embodiment depicted by FIG. 1, the frame 5 has a vertical support element 26 and a horizontal support element 30. The frame 5 also has one or more arms 34, each of which extends from the horizontal support element 30 through a respective support plate 7 to a respective support plate 8 that is attached to a support structure, such as a wall 4 of a building or other structure. In one embodiment, the arms 34 are welded to the support plates 7, 8. Further, in one embodiment, the support plates 7 are attached to the horizontal support element 30 through one or more threaded bolts passing through the support plates 7 and the horizontal support element 30, secured by one or more threaded nuts. The support plates 8 are attached to the wall 4 through one or more bolts passing through the support plates 8 in the wall, but other techniques and configurations for attaching the arms 34 and support plates 7, 8 are possible in other embodiments. As shown by FIG. 1, a motor 21 for rotating a swing 13 is mounted on the frame 5. In the exemplary embodiment shown by FIG. 1, the motor 21 is mounted near a front end 31 of the horizontal support element 30.

As described above, there are two arms 34 extending from the horizontal support element 30 to support plates 8 anchored to a wall or other structure. The arms 34 are angled to provide support in both the horizontal and vertical directions, thereby increasing the mechanical stability of the system 1. In an exemplary embodiment, each of the arms 34 is a steel bar with square cross section, and the support plates 7, 8 are also made of steel. In other embodiments, other materials and configurations are possible.

The vertical support element 26 and the horizontal support element 30 of the frame 5 can be of any shape, made of any material with any dimension and fastened together at any angle between them. In an exemplary embodiment, each of the vertical support element 26 and the horizontal support element 30 comprises a hollow tube of square cross section and is made of steel. In addition, they may be attached to one another such that they are perpendicular to each other. In other embodiments, other configurations and materials are possible.

In an exemplary embodiment, a bracket 9 is anchored to a support structure, such as a wall of a building, and the bracket 9 is used to hold the vertical support element 26 with the horizontal support element 30. In one embodiment, the bracket 9 may be an angled bracket, holding the vertical support element 26 perpendicular to the horizontal support element 30. The bracket 9 may be made of steel. The bracket 9 may be attached to the support elements 26, 30 through one or more threaded thru-bolts and nuts passing through the bracket 9 and the support elements 26, 30. The bracket 9 may be attached to a support structure, such as a wall 4, by one or more bolts passing through the bracket 9. In other embodiments, the bracket 9 may be made of other materials and have other configurations and may be attached to the wall 4 and the support elements 26 and 30 by other techniques (e.g., screws, or other coupling devices).

In an exemplary embodiment depicted by FIG. 1, the vertical support element 26 is attached to the base 6 of the frame 5 on a bottom end 29 of the vertical support element 26, and one or more support elements 3 are attached between the base 6 of the frame 5 and the vertical support element 26 near the bottom end 29 of the vertical support element 26. The base 6 of the frame 5 rests on and may be attached to a floor. The vertical support element 26 may be welded to the base 6 of the frame 5, the support elements 3, which are positioned on opposite sides of the vertical support element 26, and the base 6 of the frame 5 may be bolted or otherwise coupled to the floor. In other embodiments, other configurations and techniques for interconnecting the frame 5 and base 6 are possible. The base 6 and the support elements 3 may be made of steel or other high-strength materials. Further, in the embodiment shown by FIG. 1, the base 6 of the frame 5 is a plate with rectangular cross section, and the support elements 3 are hollow tubes with square cross section. In other embodiments, other materials and configurations of the frame 5 and base 6 are possible.

The frame 5 is coupled to and provides mechanical support for a swing 13. In this regard, the swing 13 is mounted on a seating mount 11 that is attached to and supported by the frame 5. In the embodiment shown by FIG. 1, the seating mount 11 is attached to the horizontal support element 30 near its front end 31. The seating mount 11 can be of any shape and any material. In the shown embodiment, the seating mount 11 is a stainless-steel eye bolt suspended from an underside of the horizontal support element 30. In other embodiments, other configurations of the seating mount 11 are possible, and the seating mount 11 may be attached to the frame 5 at other points. In one embodiment, a top end 14 of the swing 13 is attached to a tether 15 and a swing connector 16, which connects the swing 13 to the seating mount 11. In the shown embodiment, the tether 15 is a steel chain, and the swing connector 16 is a locking carabineer. In other embodiments, other configurations of the tether 15 and the swing connector 16 are possible, and other techniques may be used to attach the swing 13 to the frame 5.

The swing 13 can made of any material and of any color. In the exemplary embodiment shown by FIG. 1, a hammock swing is used, although other types of swings may be used in other embodiments. The hammock swing 13 of FIG. 1 includes a seat 18 and an enclosure 19 connecting the seat 18 with the top end 14 of the swing 13. The enclosure 19 has a slit 20 which provides access to an interior of the enclosure 19. In this regard, a user (e.g., a child with ASD) may enter the enclosure 19 through the slit 20, on the seat 18 and lean on the enclosure 19 during operation. The material of the enclosure 19 may be a fabric, such as cotton so that it is soft and flexible.

The motor 21 receives electrical power from a power supply, such as a wall outlet, and a controller 23 (FIG. 9) electrically controls the motor 21. When the motor 21 is actuated by the controller 23, the motor 21 converts electrical energy to mechanical energy causing a motor shaft 24 to rotate. Further, the swing 13 is indirectly engaged with the motor shaft 24, as will be described in more detail below, so that rotation of the motor shaft 24 causes the swing 13 to rotate as well. Once the motor 21 is stopped by the controller 23, the motor 21 stops rotating the motor shaft 24 and in turn the swing 13 stops rotating. In an exemplary embodiment, the motor 21 is a brushless gear motor with an ability to receive alternating current (AC) input, with a motor shaft 24 speed capacity of about 50 revolutions per minute (RPM). In some embodiments, a motor 21 that creates relatively low noise may be selected since loud noise can be disruptive to an autistic child using the swing 13 or other users. In other embodiments, other types of motors and motor speeds can be used.

Figure 2:
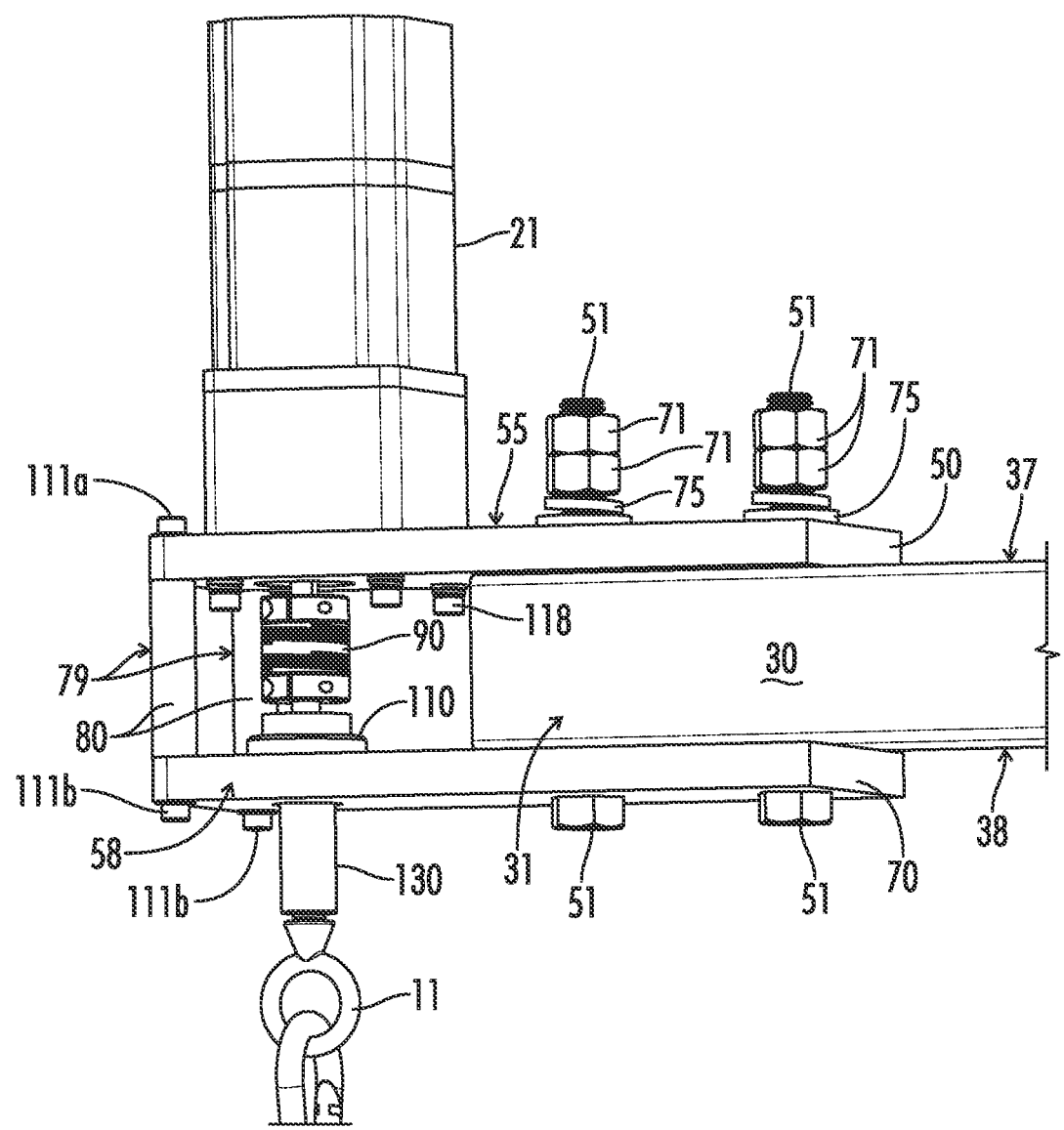
FIG. 2 depicts an exemplary embodiment of a motor mounting assembly of a rotational swing system, such as is depicted by FIG. 1.
Figure 3:
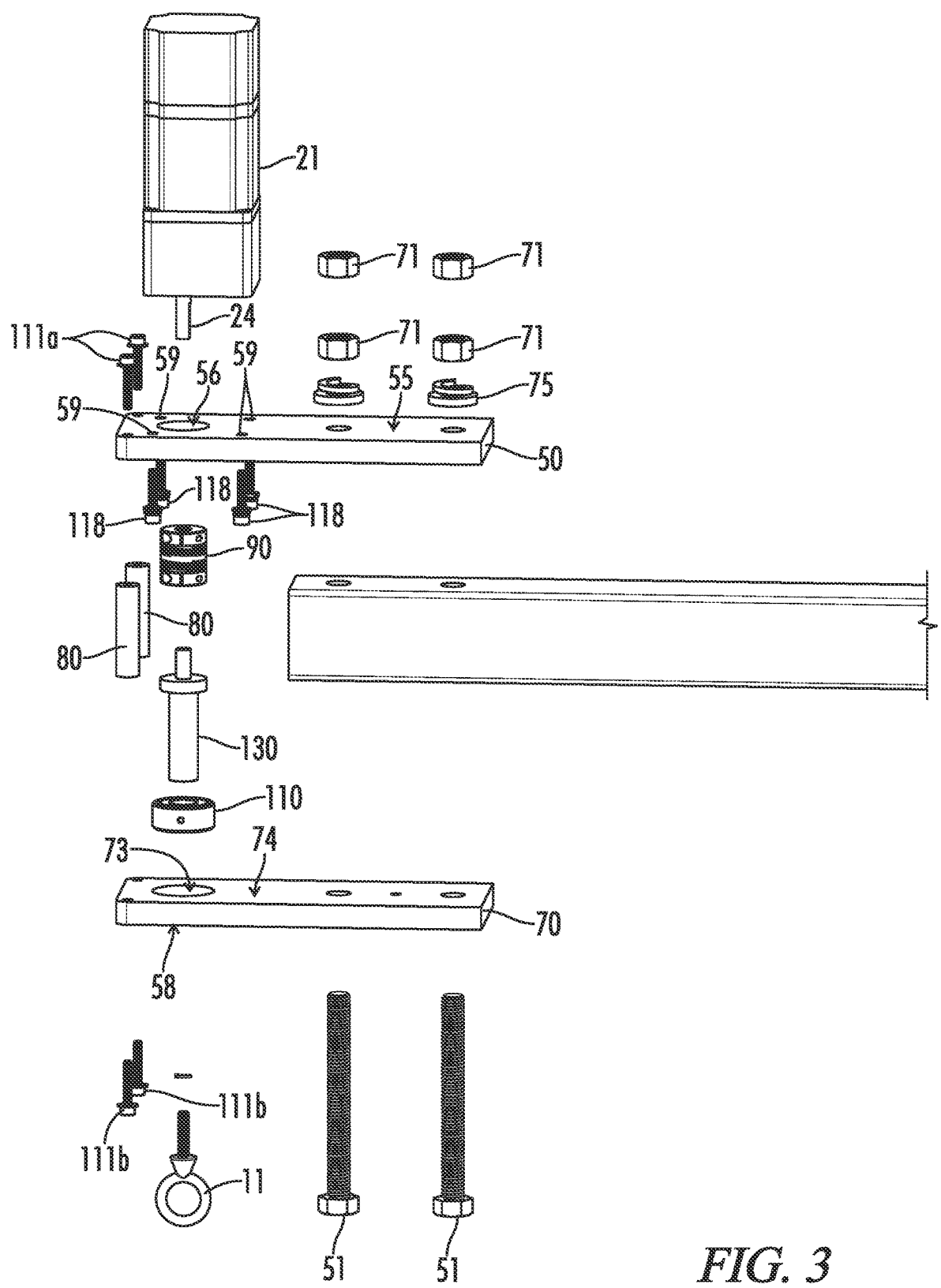
FIG. 3 depicts an exploded view of the motor mounting assembly depicted by FIG. 2.

FIGS. 2 and 3 show an exemplary assembly of the components for use in mounting the motor 21, as well as supporting and rotating the hanging load. These components include in part a support element 50, a support element 70, a coupler 90, a bearing 110 and a connector 130. In some embodiments, the support element 50 forms a plate and shall be referred to hereafter as "upper bearing plate" for simplicity of illustration, and the support element 70 forms a plate and shall be referred to hereafter as "lower bearing plate" for simplicity of illustration. In other embodiments, other configurations and shapes of the support elements 50 and 70 are possible.

In the embodiment shown by FIG. 2, the upper bearing plate 50 is placed on a top surface 37 of the horizontal support element 30 proximate its front end 31, such that an extension portion 57 of the upper bearing plate 50 extends away from the horizontal support element 30 as shown. The lower bearing plate 70 is placed on a bottom surface 38 of the horizontal support element 30 proximate its front end 31, such that an extension portion 58 of lower bearing plate 70 extends away from the horizontal support element 30 as shown. The upper bearing plate 50 and the lower bearing plate 70 can be attached to the horizontal support element 30 of the frame 5 by any suitable techniques. In the shown embodiment, the upper bearing plate 50 and the lower bearing plate 70 are both attached with one or more threaded bolts 51 and nuts 71 such that each threaded bolt 51 passes through the upper bearing plate 50, the horizontal support element 30 and the lower bearing plate 70 and is secured by at least one respective threaded nut 71. If desired, there may be a washer 75 between the upper bearing plate 50 and a respective nut 71.

In an exemplary embodiment, the motor 21 is mounted vertically on a top surface 55 of the upper bearing plate 50, such that the motor shaft 24 extends from a bottom of the motor 21. The motor shaft 24 passes through a hole 56 in the upper bearing plate 50 and is inserted into an end of the coupler 90. The other end of the coupler 90 receives one end of the connector 130, thereby connecting the motor shaft 24 with the connector 130. The coupler 90, thus, ensures that rotational motion is transferred from the motor shaft 24 to the connector 130. The bearing 110 sits on a top surface 74 of the lower bearing plate 70. A lower end 131 of the connector 130 passes through the bearing 110 and the lower bearing plate 70. The lower end 131 of the connector 130 is connected to the seating mount 11, to which the swing 13 is attached. Thus, rotation of the motor shaft 24 by the motor 21 causes rotation of the connector 130, which in turn rotates the seating mount 11 and, therefore, the swing 13. Thus, the rotary motion is transferred axially downwards from the motor shaft 24 through the connector 130 to the swing 13, enabling the swing 13 to rotate in a horizontal plane.

Figure 4A:
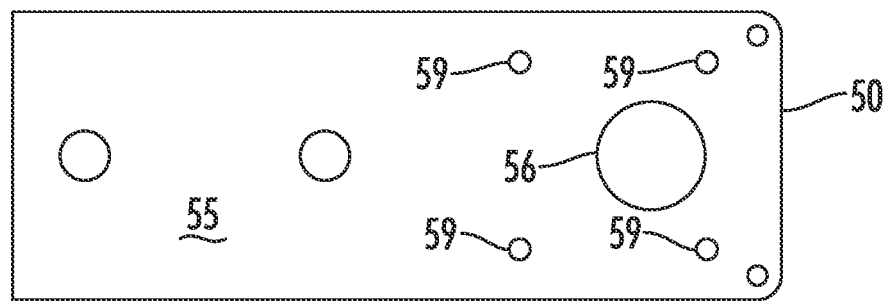
FIG. 4a depicts a top view of an upper bearing plate for a rotational swing system, such as is depicted in FIG. 1.
Figure 4B:
Figure 5A:
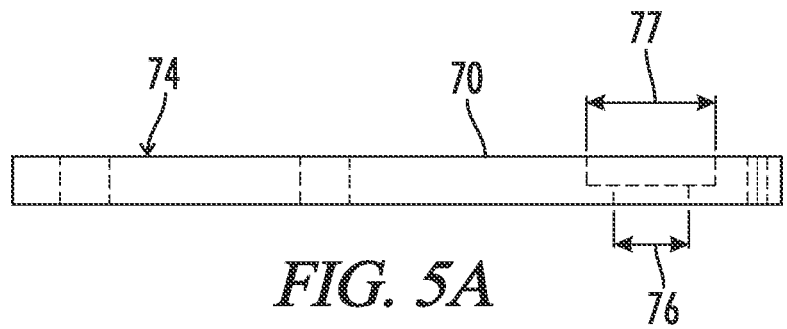
FIG. 5a depicts a side view of a lower bearing plate for a rotational swing system, such as is depicted by FIG. 1.
Figure 5B:
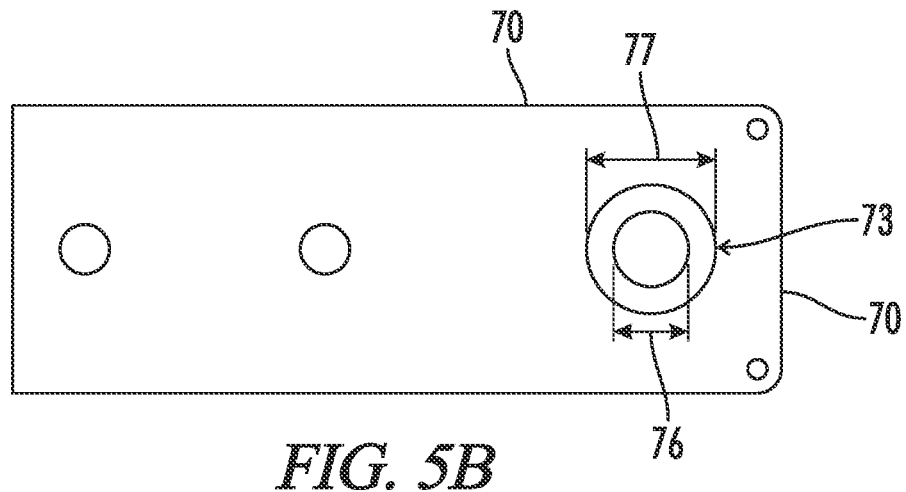

FIGS. 4a and 4b depict the upper bearing plate 50 and FIGS. 5a and 5b depict the lower bearing plate 70. The upper bearing plate 50 and the lower bearing plate 70 may be composed of steel and may form a plate of rectangular cross-section, although other materials and shapes are possible in other embodiments. The motor 21 mounted on the top surface 55 of the upper bearing plate 50 may be attached to the upper bearing plate 50 with one or more screws 118 passing respectively through one or more holes 59 in the upper bearing plate 50, although the motor 21 can be attached to the upper bearing plate 50 through other techniques in other embodiments.

The lower bearing plate 70 has a counterbore 73 running from its top surface 74 on the extension portion 58 of the lower bearing plate 70. The major diameter 77 of the counterbore 73 is at the top 74 of the lower bearing plate 70. The minor diameter 76 of the counterbore 73 is at the bottom 72 of the lower bearing plate 70 on the extension portion 58 of the lower bearing plate 70. The minor diameter 76 of the counterbore 73 should be large enough to receive the connector 130 and permit free rotation of the connector 130 within the counterbore 73. As the motor 21 begins to rotate the swing, forces are generated that act on the components supporting the motor 21 and swing 13, including the upper bearing plate 50 and the lower bearing plate 70. Such forces tend to cause the upper bearing plate 50 and the lower bearing plate 70 to deflect from their original positions, which could undesirably result in relative movement between the upper bearing plate 50 and the lower bearing plate 70. In this regard, relative movement between the plates 50 and 70 causes the separation distance between the plates 50 and 70 to change, and any change to the separation distance could add stress to the components connecting the motor 21 to the swing 13, particularly the motor shaft 21.

To prevent these additional stresses on the motor shaft 24, additional constraint is added by connecting the upper bearing plate 50 and the lower bearing plate 70 together on one end of the upper bearing plate 50 and the lower bearing plate 70 using connectors 79 as shown. In one embodiment, the connectors 79 may comprise hollow cylindrical rods 80 and may be composed of steel or some other material. In some embodiments, the rods 80 may be threaded on the inside to securely receive threaded screws 111a, as described in more detail below, in order to secure the rods to the plates 50 and 70. In other embodiments, other types of connectors 79 are possible.

In the depicted embodiment, each connector 79 is secured to the plates 50 and 70 using an upper threaded screw 111a that is inserted into a rod of the connector 79 through the upper bearing plate 70 and a lower threaded screw 111b that is inserted into a rod of the connector 79 through the lower bearing plate 50. The screw 111a presses against the upper bearing plate 70 causing the plate 70 to press against the connector's rod 80 in a downward direction. The screw 111b presses against the lower bearing plate 50 causing the plate 50 to press against the connector's rod 80 in an upward direction. The forces applied to the plates 50 and 70 by the screws and rods of the connectors 79 keep the plates 50 and 70 stationary with respect to one another such that the separation distance between the plates is constant despite the presence of fluctuating forces caused by other components, such as the forces resulting from swinging motions of the swing. In other embodiments, other techniques and types of connectors for securing the plates 50 and 70 are possible. Note that by keeping the distance between the plates 50 and 70 constant, stress on the components that connect the motor 21 to the swing 13 may be reduced, particularly the motor shaft 24.

A function of the upper bearing plate 50 is to support the motor 21, and a function of the lower bearing plate 70 is to ensure that the weight of the swing 13 is supported by the frame 5, not the motor shaft 21. By preventing the motor shaft from having to support the weight of the swing 13 and also preventing stresses that would otherwise be generated by relative movement of the upper and lower bearing plates 50 and 70, the design of the system allows for the use of relatively inexpensive motor 21, thereby significantly reducing the overall cost of the system 1.

Figure 6A:
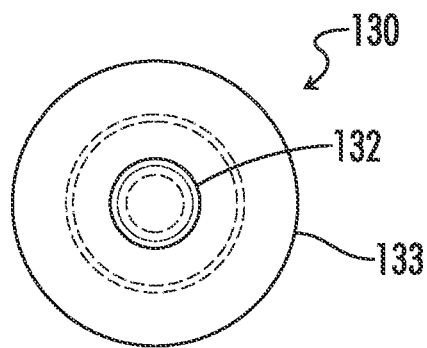
FIG. 6a depicts a top view of a connector for a rotational swing system, such as is depicted by FIG. 1.
Figure 6B:
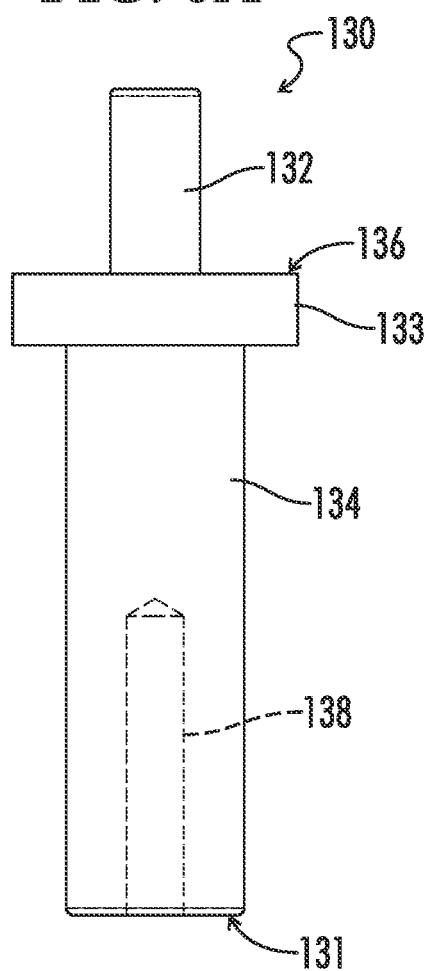
Figure 6C:
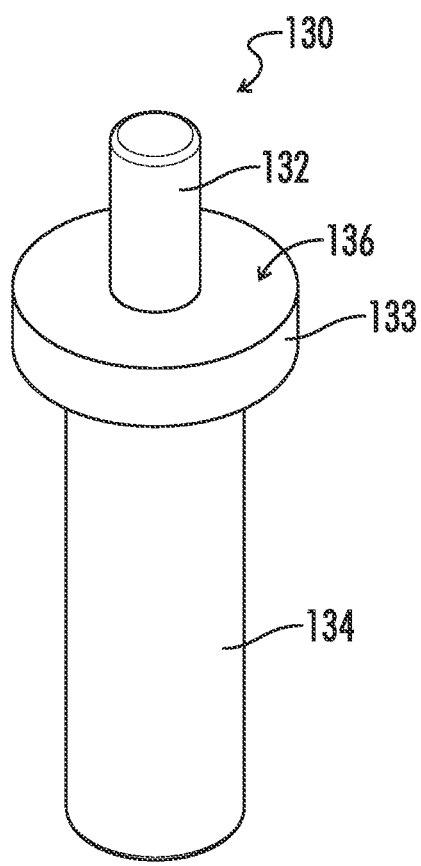
FIG. 6c depicts a three-dimensional perspective view of the connector depicted by FIGS. 6a and 6b.

FIGS. 6a, 6b and 6c depict a top view, side view and 3-dimensional perspective view of the connector 130 for the embodiment depicted in FIG. 1. In the depicted embodiment, the connector 130 includes an upper shaft 132, a neck 133 and a lower shaft 134. The upper shaft 135 of the connector 130 may be a solid cylindrical portion extending from a top surface 136 of the neck 133. The neck 133 may be a solid cylindrical body, resting on the bearing 110. The coupler 90 (FIG. 3) rests on the top surface 136 of the neck 133, so that the upper shaft 132 of the connector 130 is inserted into the coupler 90 and engages with the motor shaft 24. As an example, the upper shaft 132 and the motor shaft 24 may be sized to snugly fit in the coupler 90 such rotational movement of the motor shaft 24 is transferred to the upper shaft 132 and, thus, the connector 130 through the coupler 90. The lower shaft 134 of the connector 130 may be an elongated solid cylindrical body extending from the neck 133 through the bearing 110 (FIG. 3) and the counterbore 73 of the lower bearing plate 70 and extending away from the bottom 72 of the lower bearing plate 70. In such embodiment, the connector 130 may be a solid steel cylinder machined to form different parts of the connector 130 with varying diameters wherein the diameter of the neck $d_n$ is higher than the diameter of the lower shaft $d_l$, which in turn is higher than the diameter of upper shaft $d_u$, although in other embodiments the connector 130 can be made of other materials and be configured differently. The lower shaft 134 has an elongated hole 138 that runs from the underside 131 of the lower shaft 134, as shown. A function of the elongated hole 138 is to receive the seating mount 11 of the system 1, which is held by the connector 130. The coupling of the seating mount 11 with the connector 130 can be done through any means. The diameter of the elongated hole 138 should ensure proper coupling of the seating mount 11 with the connector 130 holds the seating mount 11 (and hence the swing 13) firmly. In the depicted embodiment, the elongated hole 138 is threaded to receive the threaded screw of the seating mount 11, whereas other embodiments may have other possible attachment techniques.

Figure 7B:
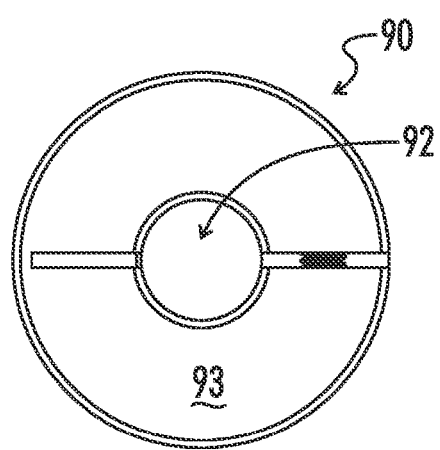
Figure 7A:
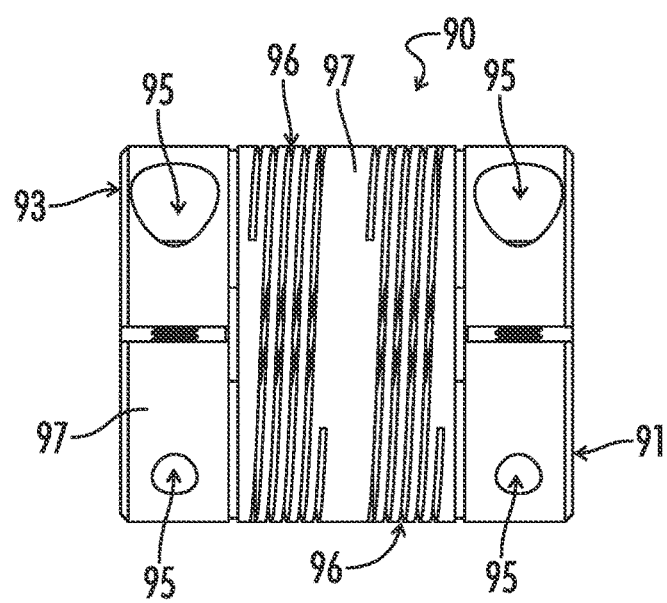
FIG. 7a depicts a side view of a coupler for a rotational swing system, such as is depicted by FIG. 1.

FIGS. 7a and 7b depict the side view and top view of the coupler 90 respectively. A function of the coupler 90 is to connect the motor shaft 24 and the connector 130 so that rotational motion is transferred from the motor shaft 24 to the connector 130 through the coupler 90. In an exemplary embodiment, helical flexible coupler is used for the coupler 90. The helical flexible coupler 90 is a flexible beam of helical shape with spiral cuts 96 along the body 97 of the coupler 90. In one embodiment, the coupler 90 is composed of aluminum whereas in other embodiments it may be composed of other materials. The coupler 90 has a bore 92 that runs from a top surface 93 of the coupler 90 to a bottom surface 91 of the coupler 90. The bottom surface 91 of the coupler 90 sits on the top surface 136 of the neck 133 of the connector 130. The motor shaft 24 is received into the bore 92 of the coupler 90 through the top surface 93 of the coupler 90, and the connector 130 is received into the bore 92 of the coupler 90 through the bottom surface 91 of the coupler 90, thus engaging the motor shaft 24 and the connector 130. The diameter of the bore 92 should be sufficiently large to hold the motor shaft 24 and the connector 130. The coupler 90 allows small misalignment between the motor shaft 24 and the connector 130, such as angular misalignment, parallel misalignment and axial misalignment, wherein the spiral cuts 96 of the coupler 90 help in accommodating misalignment without applying significant force to the motor shaft 24 resulting from the misalignment. In the shown embodiment, the coupler 90 may allow a parallel misalignment of up to about 0.01 inch, an angular misalignment of up to about 30 degrees and an axial misalignment of up to about 0.008 inch between the motor shaft 24 and the connector 130, although other tolerances are possible in other embodiments. The coupler 90 also ensures a constant velocity across it. As an example, the velocity of the motor shaft 24 may be equal to the velocity of the connector 130.

The coupler 90 has a plurality of provisions 95 for receiving clamping screws (not shown) to adjust the inner diameter of the connector 130 at each end. In this regard, clamping screws may be pressed against the coupler 90 at the provisions 95 in order to tighten the coupler 90 around the motor shaft 24 inserted into the coupler 90 at one end and also to tighten the coupler 90 around a shaft of the connector 130 inserted into the coupler 90 at the other end. Frictional forces between the coupler 90 and the components (i.e., the motor shaft 24 and the connector 130) inserted into the coupler 90 may prevent relative movement of such component so that rotational movement of the motor shaft 24 is transferred to the connector 130.

Figure 8B:
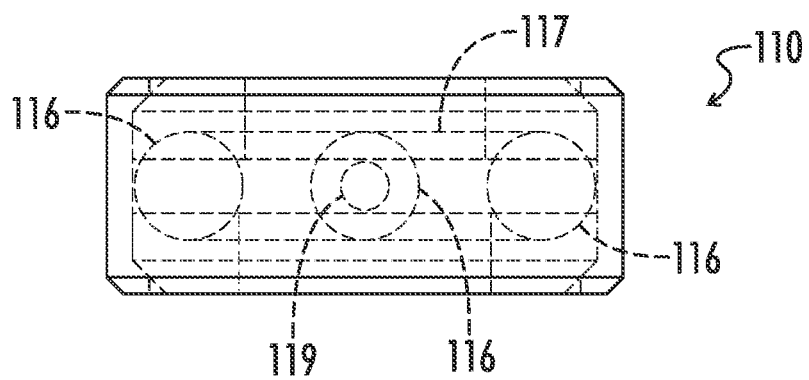
Figure 8A:
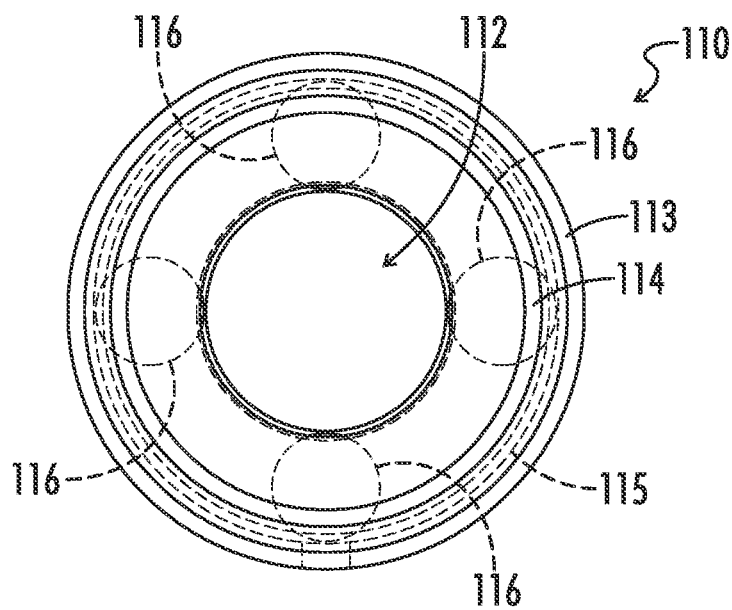
FIG. 8a depicts a top view of a bearing for a rotational swing system, such as is depicted by FIG. 1.

FIGS. 8a and 8b depict the front view and top view of the bearing 110 respectively. A function of the bearing 110 is to permit rotation between parts and to support the axial loading. The bearing 110 further provides free motion to a rotating part by reducing friction. In an exemplary embodiment depicted, a thrust ball bearing made of steel is used, although in other embodiments any other bearing and material can be used. The bearing 110 includes an outer ring 113, an intermediate layer 115 and an inner ring 114. The intermediate layer 115 defines a cage 117 for housing and connecting a plurality of balls 116. The inner ring 114 and the outer ring 113 are arranged to form a guide way, which accommodates the intermediate layer 115 in between the outer ring 113 and the inner ring 114. The diameter $d_o$ of the outer ring 113 is larger than the diameter $d_b$ of the intermediate layer 115, which in turn is larger than the diameter $d_i$ of the inner ring 114. The outer ring 113 remains stationary and rests on the counterbore 73 of the lower bearing plate 70. The intermediate layer 115 rotates along the guideway between inner ring 114 and the outer ring 113 with the help of a plurality of balls 116. The inner ring 114 rotates along with the intermediate layer 115. The lower shaft 134 of the connector 130 is inserted through a bore 112 running through the bearing 110. As the motor 21 is actuated and the rotational motion is axially transferred downwards from the motor shaft 24, the inner ring 114 and the intermediate layer 115 rotate when the connector 130 rotates, thus helping in rotation and free motion between parts. The Diameter $d_{bo}$ of the bore 112 is selected to ensure proper assembly of the connector 130 with the bearing 110. The bearing 110 is press-fit on the major diameter 77 of the counterbore 73 of the lower bearing plate 70 with a tight tolerance. In such embodiment, one or more oil holes 119 may be available on the bearing 110, for lubrication purposes.

Figure 9:
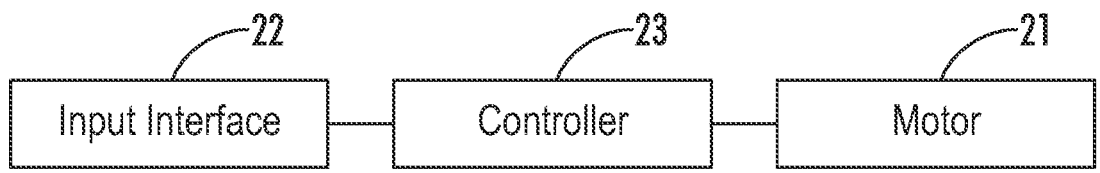
FIG. 9 is a block diagram illustrating a control system of a rotational swing system, such as is depicted by FIG. 1.

FIG. 9 is a block diagram depicting components involved in operation and control of the motor. An input interface 22 receives inputs that may be used to set input parameters for controlling the swing 13, and the input interface 22 transmits such inputs to the controller 23, which then controls the operation of the motor 21, such as speed, direction, and duration of rotation, based on the inputs. In some embodiments, the input interface 22 comprises buttons, switches, dials, and/or other types of devices typically used to receive input from users. In some embodiments, the input interface 22 comprises a display screen for displaying information to a user and a keypad to receive inputs. In other embodiments, the input interface 22 may comprise a touchscreen capable of both displaying information and receiving inputs through touches of the touchscreen. In other embodiments, other types of user interfaces may be used. As an example, the input interface may include a wireless communication device for receiving inputs wirelessly, such as from a smartphone or other wireless device. In such example, a person sitting in the swing 13 or at a remote distance from the swing 13 may operate the swing 13 by submitting inputs to an electronic device that wirelessly transmits the inputs to the input interface 22.

In an exemplary embodiment, the input interface 22 contains switches including a power switch, emergency switch, a speed dial and a timer dial for controlling the operation of the motor 21. Other types of switches or other input interfaces are possible in other embodiments.

The controller 23 may include integrated circuits such as one or more logic circuits (e.g., a field programmable gate array), microcontrollers, and microprocessors for controlling operation of the motor 21. In some embodiments, the controller 23 may perform pre-defined functions of the motor such as running for a set speed, time and rotational direction (clockwise or counterclockwise) by executing a set of codes or instructions or programs written and stored on a memory device. That is, the controller 23 may have one or more processors programmed with computer code for performing the functions described herein for the controller 23. In some embodiments, there may be additional sensors deployed to provide feedback to the controller 23, which may then adjust its control of the motor 21 accordingly.

Figure 10:
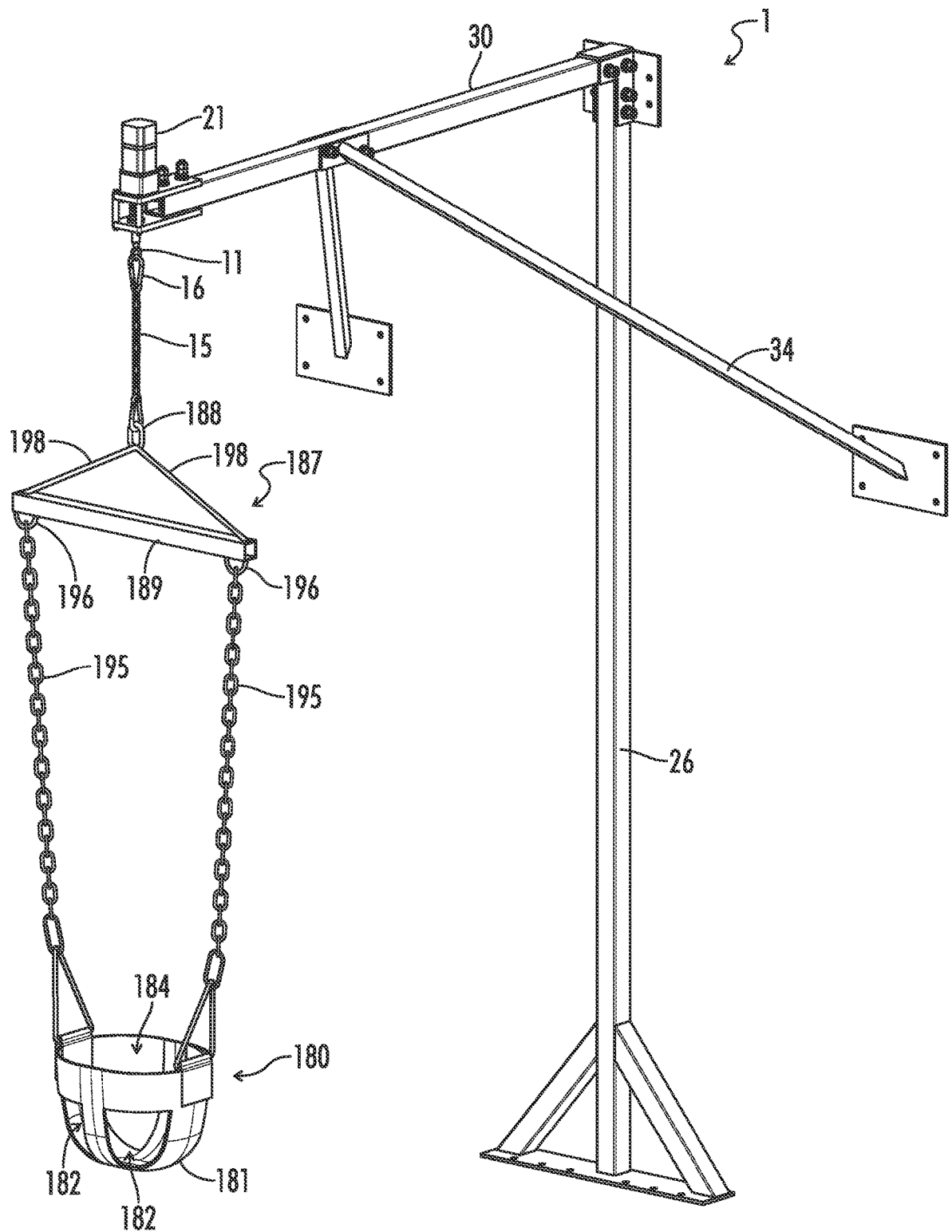
FIG. 10 depicts an exemplary embodiment of a bucket swing for a rotational swing system.

FIG. 10 depicts another exemplary embodiment of the rotational swing system 1. This embodiment has features that are similar to the aforementioned embodiment depicted in FIG. 1. However, in FIG. 10, the system comprises a bucket swing 180 rather than a hammock swing, as shown by FIG. 1. The bucket swing 180 includes a seat enclosure 181 to accommodate a person, an open top 184 providing access to the seat enclosure 181 for a person to sit, and a plurality of openings 182 through a bottom 185 of the bucket swing 180 for insertion of a person's legs while sitting on the seat enclosure 181. The setup 1 further includes a two-point seating adapter 187. The two point seating adapter 187 includes a locking element 188 to connect and lock the seating adapter 187 with the seating mount 11 of the system 1, a crossbar 189 that is connected to the locking element 188 on both sides of the crossbar 189 through a plurality of support rods 198, as shown. Two hooking points 196 are attached on either side of the crossbar 189 from the underside of the crossbar 189. The bucket swing 180 is suspended from the hooking points 196 of the seating adapter 187 by suspension connectors 195 connected to the hooking points 196.

In the depicted embodiment, the crossbar 189 is a steel beam of rectangular cross-section, the suspension connectors 195 are steel chains, and each of the hooking points 196 is a stainless steel eye bolt. In other embodiments, the aforementioned parts can be made of other materials and shapes, and other types of components for the swing 180 are possible.

Now, therefore, the following is claimed:

1. A rotational swing system for providing vestibular stimulation, comprising:
    a plurality of support elements, including at least a first support element and a second support element;
    a motor mounted on the first support element, the motor having a motor shaft;
    a first connector having a head resting on the second support element;
    a coupler coupled between the connector and the motor shaft;
    a seating mount coupled to the connector;
    a swing coupled to the seating mount,
    wherein the motor is configured to rotate the motor shaft such that rotational movement of the motor shaft is transferred through the coupler, the connector, and the seating mount to the swing, and wherein a weight of the swing causes the head to press against the second support element.

2. The system of claim 1, wherein the plurality of support elements further include a third support element, and wherein the second support element is coupled to the third support element.

3. The system of claim 2, wherein the third support element is coupled to a wall of a building.

4. The system of claim 2, wherein the first support element forms a first plate, and wherein the first connector passes through the first plate.

5. The system of claim 4, wherein the second support element forms a second plate, and wherein the system further comprises a second connector for coupling the first plate to the second plate.

6. The system of claim 1, wherein the first connector has a first shaft passing through the coupler.

7. The system of claim 6, wherein the first connector has a second shaft opposite of the first shaft, and wherein the second shaft is coupled to the seating mount.

8. The system of claim 7, wherein the head has a first surface and a second surface that is opposite of the first surface, and wherein the first shaft extends from the first surface, and wherein the second shaft extends from the second surface.

9. The system of claim 7, wherein the second shaft has a hole for receiving a portion of the seating mount.

10. The system of claim 9, wherein a wall of the hole is threaded.

11. A swinging system for providing vestibular stimulation, comprising:
    a frame;
    a motor having a motor shaft;
    a first connector having a first shaft;
    a coupler for coupling the motor shaft to the first shaft;
    a seating mount coupled to the first connector; and
    a swing coupled the seating mount,
    wherein the first connector is positioned on the frame such that a weight of the swing causes the first connector to press against a surface of the frame, and wherein the motor is configured to rotate the motor shaft such that rotational movement of the motor shaft is transferred through the first connector, the coupler, and the seating mount to the swing.

12. The system of claim 11, wherein the first connector has a head that presses against the surface of the frame.

13. The system of claim 12, wherein the first connector has a second shaft coupled to the seating mount.

14. The system of claim 13, wherein a portion of the seating mount is inserted into the second shaft.

15. The system of claim 14, wherein the first shaft is opposite of the second shaft.

16. The system of claim 11, wherein the frame has a first plate on which the first connector is positioned, wherein the frame has a second plate on which the motor is positioned, and wherein the system further comprises a second connector for connecting the first plate to the second plate.

17. The system of claim 16, wherein the second connector secures the first plate to the second plate such that relative movement between the first plate and the second plate is prevented.

18. A method for providing vestibular stimulation to a user, comprising:
    positioning the user in a swing that is coupled to a motor through a seating mount, a first connector, and a coupler, wherein the first connector is coupled between the coupler and the seating mount, wherein the coupler is coupled between the first connector and a motor shaft of the motor, wherein the motor is mounted on a first support element and the first connector has a head resting on a second support element such that a weight of the swing is supported by the first support element; and
    driving the motor, thereby rotating the motor shaft such that rotational movement of the motor shaft is transferred through the coupler, the first connector, and the seating mount to the swing.

19. The method of claim 18, wherein the first support element forms a first plate, and wherein the first connector passes through the first plate.

20. The method of claim 19, wherein the second support element forms a second plate, and wherein a second connector couples the first plate to the second plate.

21. The method of claim 18, wherein the first connector has a first shaft passing through the coupler.

22. The method of claim 21, wherein the first connector has a second shaft opposite of the first shaft, and wherein the second shaft is coupled to the seating mount.

23. The method of claim 22, wherein the head has a first surface and a second surface that is opposite of the first surface, and wherein the first shaft extends from the first surface, and wherein the second shaft extends from the second surface.

24. The method of claim 22, wherein the second shaft has a hole into which a portion of the seating mount is inserted.

25. The method of claim 24, wherein a wall of the hole is threaded.

\* \* \* \* \*